United States Patent [19]

Kirsch

[11] Plant 4,906

[45] Oct. 26, 1982

[54] LILY NAMED TEMPO

[75] Inventor: Ted T. Kirsch, Myrtle Point, Oreg.

[73] Assignee: Sun Valley Bulb Farms, Inc., Myrtle Point, Oreg.

[21] Appl. No.: 215,233

[22] Filed: Dec. 11, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—C. W. Rummler

[57] ABSTRACT

A new and distinct variety of lily plant of the Parkmannis-type oriental hybrid particularly distinguished by the glossy purple red coloring and white frilly border of its 7 to 8 inch diameter, generally flat, outwardly facing flowers which are borne with raceme arrangement on long, strong stems which carry stiff, upwardly extending pedicels, usually with one bud or flower on each pedicel, and by its dark green, glossy and relatively disease-resistant foliage.

2 Drawing Figures

BACKGROUND OF THE NEW PLANT

This new variety of lily plant originated as a seedling of unknown parentage growing at my nursery in Arcata, Calif. Its relatively disease-resistant, brilliantly colored, flat, outwardly facing flowers and green, glossy foliage prompted me to asexually propagate this new plant for study with the result that I have found advantageous and distinctive characteristics in the new plant which make it a valuable addition to the field of commercial lily culture for cut flower production. Propagation of this new lily plant through successive generations by means of scales and tissue culture at Arcata, Calif., has shown that its distinctive characteristics hold true from generation to generation and appear to be firmly fixed.

DESCRIPTION OF THE DRAWING

This new variety of lily plant is illustrated by the accompanying photographic drawing which, in full color, shows a full grown blooming plant in the upper view and a close-up of several blooms in the lower view, the color rendition being as nearly true as can be obtained by conventional photographic procedures.

DESCRIPTION OF THE NEW PLANT

The following is a detailed description of this new variety of lily plant as observed in the summer of 1980 on field grown plants at Arcata, Calif. The color designations are according to the R.H.S. Colour Chart published by The Royal Horticultural Society of London, England.

THE PLANT

Origin: Seedling.

Parentage: Unknown.

Classification: Oriental Hybrid-Parkmannis.

Form: Tall single stem from each bulb.

Height: 2½ to 4 feet at maturity.

Growth: Sturdy and upright with excellent strength.

Cane size: Stems grow from ⅛ inch base diameter when at a height of 2½ feet to ¼ inch base diameter when at a height of 4 feet.

Foliage:

*Quantity.*—Abundant.

*Leaf, number and size at flower cluster.*—Three in number, varying from one at the base of each pedicel about 3½ inches long and 1⅛ inches wide, to one on the pedicel approximately 1 inch from the flower bud and about 2¾ inches long and ⅜ inch wide.

*Shape.*—Lanceolate.

*Texture.*—Leathery.

*Aspect.*—Smooth.

*Ribs and veins.*—Distinct longitudinal veins from base to tip.

Stem bulblet (underground): Occurrence — one to three on each healthy, normal plant at digging time.

*Size.*—From ¼ inch to 1 inch in diameter.

*Color.*—White, with occasional pink shading at the tips.

Bulbs:

*Size.*—From about 6 inches to 10 inches in circumference, depending on age.

*Color.*—White, with yellow and pink overtones. As bulbs become larger and older, the overtones of yellow and pink become more and more prominent.

THE BUD

Form: Generally lanceolate, with acute apex.

Size: Average; about 4 to 5 inches long and about 1 to 1½ inches in diameter.

Number: Usually one on each pedicel, with one to eight buds on a plant according to culture and bulb size.

Opening: Normal; buds open successively from the lowermost bud to the top bud, which is the last to open.

Color: When sepals are about to divide and petals begin to unfurl, dark reddish pink at the tip of the bud fading to a darker pink at the base.

Surface texture: Rugose, leathery, with prominent veins.

Pedicel: Strong and generally upright, angled about 45° from the vertical.

*Color.*—Light green on the under side and dark maroon on the top side. The pedicel is glabrous.

*Length.*—3 to 4 inches.

THE FLOWER

Blooming habit: Annually, blooming profusely in July.

Size of flower: Large, averaging 6½ to 7½ inches in diameter.

Borne: From larger bulbs, the inflorescence has a raceme arrangement with each pedicel bearing one bud. The size of the bulb and its cultural care will determine the number of blooms and buds to be found on any given inflorescence. From large bulbs, this lily may have three to six blooms open at one time.

Shape: Generally flat, with uniformly spaced petals in star arrangement and with the very tips of the petals curving slightly backward.

Petalage: Normal, three sepals and three petals.

*Form.*—Oval, with obtuse apex and a center furrow bisecting each petal longitudinally. The edges are sinuate and the petals are about 4 inches long and 3½ inches wide.

*Color.*—Upon opening, the petal is generally Red Purple RHS 60C overlaid profusely with Dark Maroon spots of RHS 60A, except for the tip portion of the petal and the slightly frilled White edge of RHS 155D which is about 1/16 to ⅛ inch wide.

*Papillae.*—Present on the petals and from 4 to 8 in number.

*Texture.*—Leathery.

*Aspect.*—Velvety.

Fragrance: Sweet.

Discoloration: The color darkens somewhat as the blossom matures.

Effect of weather: Flower generally not affected by wet weather but flower ages as temperature rises.

Persistence: The flower tends to hang on and dry.

Lasting quality:

*On the plant.*—Two to three weeks depending on the size of the bulb and its environmental temperature.

*As a cut flower.*—Ten days to two weeks.

REPRODUCTIVE ORGANS

Stamens:

*Anthers.*—Six in number, about 1 inch long, and in orderly arrangement around the pistil.

*Filaments.*—Length — about 2 inches.

*Color.*—Greenish yellow.

Pistils:

*Number.*—One.

*Style.*—Length — about 3¼ inches. Color: light green at the base and darkening somewhat at the stigma.

*Stigma.*—Color: light grey.

*Ovary.*—Classified as a schizocarp, about 3½ to 4 inches long and 1½ inches in diameter, dehiscing into thirds and containing six rows of seeds of the usual shape for lilies.

I claim:

1. A new and distinct variety of oriental hybrid lily plant substantially as herein shown and described, characterized by its large, brilliant, reddish purple, outwardly facing flowers borne on strong, stiff pedicels, and by its dark green, glossy foliage.

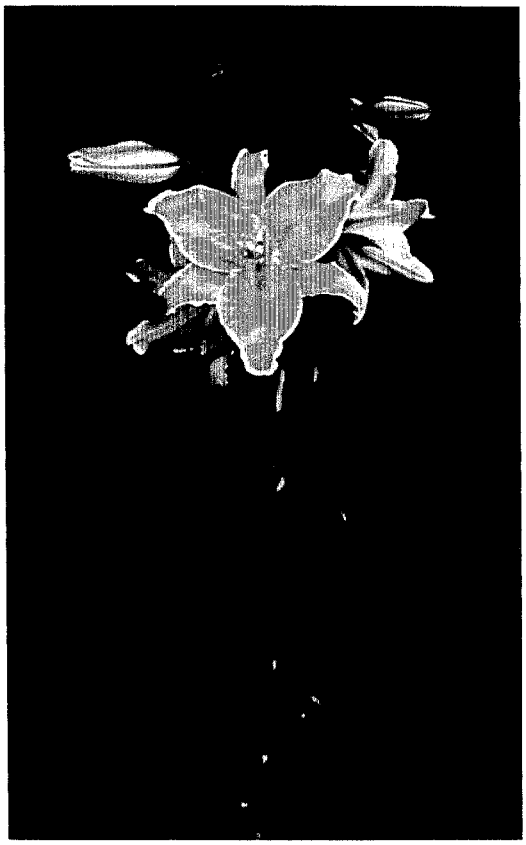
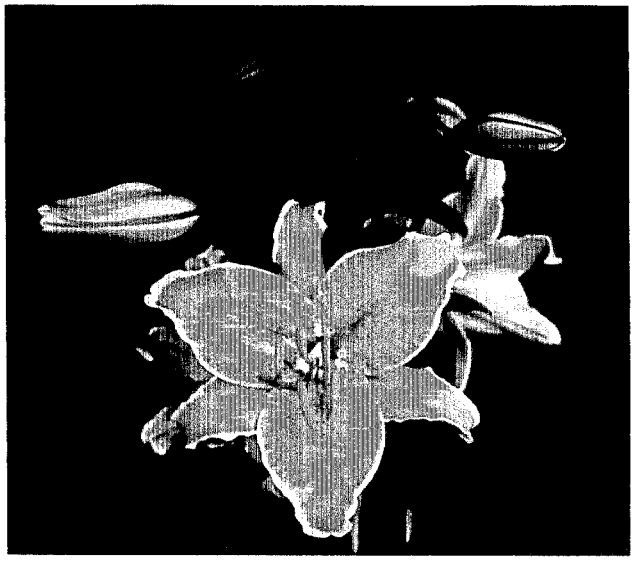

* * * * *